United States Patent [19]

Heady et al.

[11] 3,941,655

[45] *Mar. 2, 1976

[54] METHOD FOR RECOVERING XYLOSE ISOMERASE

[75] Inventors: Robert E. Heady, Park Forest; William A. Jacaway, Jr., Downers Grove, both of Ill.

[73] Assignee: CPC International Inc., Englewood Cliffs, N.J.

[*] Notice: The portion of the term of this patent subsequent to Nov. 12, 1991, has been disclaimed.

[22] Filed: Oct. 10, 1974

[21] Appl. No.: 513,910

Related U.S. Application Data

[60] Division of Ser. No. 401,757, Sept. 28, 1973, Pat. No. 3,847,740, which is a continuation-in-part of Ser. No. 294,397, Oct. 2, 1972, Pat. No. 3,847,741.

[52] U.S. Cl. .................... 195/31 F; 195/63; 195/65; 195/68
[51] Int. Cl.² C07G 7/028; C12D 13/10; C12D 13/02
[58] Field of Search ............ 195/31 F, 62, 66 R, 63, 195/68

[56] References Cited
UNITED STATES PATENTS

| | | | |
|---|---|---|---|
| 3,622,463 | 11/1971 | Iizuka et al. | 195/66 R |
| 3,775,254 | 11/1973 | Buetow | 195/68 |
| 3,847,740 | 11/1974 | Heady et al. | 195/31 F |

OTHER PUBLICATIONS

Dixon et al., Enzymes, Academic Press Inc., New York, 2nd ed., 1964, pp. 41–43.

Primary Examiner—Lionel M. Shapiro
Assistant Examiner—Thomas G. Wiseman
Attorney, Agent, or Firm—Albert P. Halluin

[57] ABSTRACT

Levulose-bearing syrups are produced by passing a dextrose solution through a column or bed of an immobilized dextrose isomerase enzyme preparation. The useful life of the enzyme preparation is extended by conducting the isomerization initially at a low operating temperature, then increasing the temperature of operation after an initial decrease in enzyme activity has been observed. Also disclosed is an improved immobilized xylose isomerase enzyme preparation which is prepared by contacting a solution of xylose isomerase with particulate basic magnesium carbonate. The novel immobilized enzyme preparation is useful in enzymatically isomerizing dextrose solutions to levulose-bearing syrups.

8 Claims, No Drawings

METHOD FOR RECOVERING XYLOSE ISOMERASE

CROSS-REFERENCE TO RELATED APPLICATIONS

This application is a division of U.S. application Ser. No. 401,757, filed Sept. 28, 1973, now U.S. Pat. No. 3,847,740, granted Nov. 12, 1974, which in turn is a continuation-in-part of U.S. application Ser. No. 294,397, filed Oct. 2, 1972, now U.S. Pat. No. 3,847,741, granted Nov. 12, 1974, the disclosure of which is incorporated herein by reference.

FIELD OF THE INVENTION

This invention relates generally to enzymatic isomerization. More particularly, the invention relates to improvements in continuous isomerization techniques.

DESCRIPTION OF THE PRIOR ART

The enzymatic hydrolysis of starch, for the production of corn syrup and corn syrup solids, is routinely conducted on a commercial scale to produce hydrolysates at D.E. values in excess of 95, utilizing what are essentially batch techniques.

The reported investigations of the enzymatic isomerization of dextrose and of starch hydrolysates, for the production of levulose-bearing products, have generally utilized batch isomerization techniques. An exemplary batch isomerization, for example, might be conducted in a stirred tank reactor at a temperature of about 70°C and at a pH of about 6.2, for an isomerization period of from about 40 to 60 hours. The enzyme dosage and conversion temperature are selected to obtain a desired levulose content in the end product. The pH of the syrup would be maintained at about 6.2, by either continuous or incremental additions of a basic material, such as sodium bicarbonate, during isomerization.

The selection of optimum operating conditions, for batch isomerization, is not easy. One initial variable that can be fixed, to some extent, is the particular enzyme preparation that is employed. Isomerase enzymes have their own individual characteristics and those derived from different microorganisms cannot be considered to have the same optimum conditions for action. For example, each enzyme preparation ordinarily will be found to have its own optimum pH, optimum temperature, metal requirement, temperature stability, and Michaelis constant, among other properties, as is reported, for example, by Dr. T. Sato, in "The Enzyme for the Isomerization of Glucose," in the Japanese publication *Dempunto Gijutsu Kenkyu Kaiho* 32, 81–88 (1965).

When the enzyme preparation is derived from a microorganism of the Streptomyces genus, the rate of levulose formation by the enzyme is much greater at 70°C than at 60°C. However, at pH 6.2, some of the advantages of conducting the isomerization at the higher temperature are lost, since the slightly acid pH reduces the rate of levulose formation and reduces enzyme stability. In fact, neither the 70°C operating temperature nor the slightly acidic pH are conducive to enzyme stability.

For effective batch isomerization, continuous mixing of the starch hydrolysate solution (syrup) is necessary. Unfortunately, when cells are used as the source of enzyme activity, the mixing action apparently imposes shear forces on the microbial cells that contain the enzyme. When cells are ruptured, the cellular fluids, including the enzyme, are released into the solution. The enzyme appears to be more susceptible to inactivation under these conditions, than enzyme that remains within intact cells.

Some consideration of the effect of temperature on isomerase has been reported in the literature. For example, two of the pioneer workers in the field, N. Tsumura and T. Sato of the Japanese Food Research Institute, published a series of papers entitled, "Enzymatic Conversion of D-Glucose to D-Fructose". In parts V and VI, which appear in *Agr. Biol. Chem.* 29, 1123–1128 and 1129–1134, respectively (1965), they describe the effects of temperature on an isomerase obtained from *Aerobacter cloacae*. They found that this enzyme lost the majority of its activity at 80°C in the presence of magnesium and at 90°C in the presence of cobaltous ion. Without the presence of stabilizing metal ions, exposure of their enzyme to a temperature of 70°C for a ten-minute period resulted in a very substantial loss of enzyme activity. The addition of stabilizing metal ions enhanced heat tolerance, but even so, enzyme inactivation could be observed at about 80°C.

An article by Yoshimura, Danno and Natake, of Hyogo University, Japan, appearing in *Agr. Biol. Chem.* 30 (10), 1015–1023 (1966), entitled "Studies on Glucose Isomerizing Activity of D-xylose Grown Cells from *Bacillus coagulans*, Strain HN-68", reports the effect of temperature on the isomerase enzyme from their source microorganism. Maximum activity after two hous incubation was observed at 70°C. Maximum enzyme activity after twenty hours incubation was observed at temperatures in the range from 60°C to 65°C. Above 70°C, substantial inactivation of the enzyme could be observed after two hours, and when operating temperatures for given enzyme dose batches were compared after twenty hours, substantial enzyme inactivation appeared to occur above 65°C.

In the *Journal of Food Science and Technology* (Nipon Shokuhin Kogei Gakkaishi) 14 (12), 539–540 (1967), N. Tsumura and M. Ishikawa, in "Continuous Isomerization of Glucose by a Column of Glucose Isomerase", described a continuous isomerization technique in which a purified isomerase enzyme sample, derived from a strain of Streptomyces, was anchored on a DEAE-Sephadex bed in a column, to immobilize the enzyme. A glucose solution was then passed through the column. The column was heated by warm water at 60°C, which was passed through a jacket. An eventual reduction in enzyme activity was observed, although the authors were not certain whether the decrease in observed isomerization was caused by enzyme inactivation or by latching of the enzyme from the column.

More recently, in a paper appearing in the text, "Fermentation Advances", edited by D. Perlman, Academic Press, 1969, beginning at page 561, Dr. Takasaki and his associates from the Japanese Fermentation Research Institute have described a continuous column isomerization and have characterized the heat stability of an isomerase enzyme derived from a particular strain of Streptomyces. They observed enzyme inactivation after ten minutes at temperatures above 70°C.

OBJECTS OF THE INVENTION

One object of the present invention is to provide new and improved practical techniques for conducting the enzymatic isomerization of dextrose to levulose on a continuous basis.

Another object of the invention is to provide practical processes for the isomerization of starch hydrolysates or dextrose solutions to levulose-bearing products, that are more attractive for commercial exploitation than prior art processes.

DEFINITIONS

Because of the plethora of terms that are in common use in the art, a few definitions are made to simplify the present application and permit it to be more concise.

D.E.: The term "D.E." is an abbreviation for "dextrose equivalent," and these terms are used interchangeably to refer to the reducing sugar content of a material calculated as dextrose and expressed as percent of total solids.

Starch Hydrolysate: The term "starch hydrolysate" is used in a general way to refer to a syrup or dry product that is made by the hydrolysis of starch. Such a product may be made by acid or enzymatic hydrolysis, or by a combination of acid and enzymatic hydrolysis. A preferred type of starch hydrolysate for use for isomerization in accordance with the present invention is produced by acid or enzyme thinning to a D.E. of 10 or less, followed by enzymatic saccharification to a D.E. above 95, and preferably above 97.5.

Glucose and Dextrose: Medium D.E. starch hydrolysates are commonly referred to in the art as "glucose," whether the starch hydrolysate is in the form of a syrup or in the form of solids. The term "dextrose" is commonly reserved for the refined crystalline monosaccharide that is recovered from a high D.E. starch hydrolysate, or for D-glucose as a constituent of starch hydrolysates. As used hereafter, the term "dextrose" will be used to embrace this monosaccharide in any form, in solution or dry, as a constituent of a starch hydrolysate syrup, syrup solids, or in refined crystalline form.

Fructose and Levulose: The terms "fructose" and "levulose" are generally employed interchangeably in the art to refer to a particular isomer of dextrose that is sweeter than dextrose. This isomer is found in honey and in invert sugar, along with dextrose, and it is valuable because of its sweetness. The term "levulose" will be used to refer to this monosaccharide.

The enzyme: The enzyme that isomerizes dextrose to levulose has been referred to in the art by several names. It is referred to in the Marshall U.S. Pat. No. 2,950,228, as xylose isomerase, because it isomerizes xylose to xylulose. This activity is in addition to its ability to isomerize dextrose to levulose. It has also been referred to in the art as dextrose isomerase and glucose isomerase. The term "xylose isomerase" will be used herein, since investigations have revealed that xylose is the natural substrate of the isomerase.

Enzyme preparation: The term "enzyme preparation" is used to refer to any composition of matter that exhibits the desired xylose isomerase enzymatic activity. The term is used to refer, for example, to live whole cells, dried cells, cell extracts, and refined and concentrated preparations derived from the cells. Enzyme preparations may be either in dry or liquid form. Since this invention is concerned with continuous processes, the enzyme preparation will always be employed in some immobilized form. For example, the enzyme preparation may be dispersed in a starch hydrolysate solution, but may be retained in that solution, while desired end products are selectively permitted to discharge from the solution through a selective membrane by ultrafiltration techniques. Alternatively, the enzyme preparation may be bound to an insoluble matrix. The three principal methods for binding enzymes to matrices are by ordinary covalent chemical linkages, by adsorption, and by entrapment of the enzyme within a gel lattice having pores large enough to allow the molecules of the the substrate and of the product to pass freely, but small enough to retain the enzyme.

Units: All parts and percentages are by weight, and on as is basis, unless expressly stated to be otherwise.

Isomerase unit: One isomerase unit is defined as the amount of enzyme activity that is required to produce one micromole of levulose per minute under the isomerization conditions described hereafter under the heading, "Assay of Isomerase Activity."

Streptomyces: This term refers to a genus of microorganisms of the order of Actinomycetales. These microorganisms are aerial mycelium-producing actinomycetes. The genus is well recognized. Some of its important distinguishing characteristics are described, for example, in the text, "The Actinomycetes," by Selman A. Waksman, The Ronald Press Company, New York, 1967, page 135 et seq.

BRIEF SUMMARY OF THE INVENTION

We have now discovered a practical, continuous process for the isomerization of dextrose to levulose that has several attendant advantages.

Generally, the process of the invention involves conducting the isomerization at an initial, fairly constant temperature of at least 50°C, followed by increasing the operating temperature, either in several increments or in a single step, to a value that is 5°C or more higher than the initial operating temperature, to an operating temperature not exceeding 80°C.

In greater detail, in one preferred mode for practicing the invention, the process involves subjecting a stream of a solution containing dextrose to the action of an immobilized enzyme preparation at a pH of at least 7.0 and preferably in the range from pH 7.5 to 8.5, and at a temperature level of at least 50°C but that is at least 10°C below the temperature at which rapid inactivation of the enzyme occurs, during an initial isomerization phase. For enzyme preparations derived from microorganisms of the Streptomyces genus, ordinarily the temperature above which rapid inactivation of the enzyme preparation can be observed is about 70°C, so that the preferred operating temperature during the initial phase of isomerization is about 60°C or lower, that is, preferably 50°C to 60°C. At temperatures in the range from 50°C to 60°C, some enzyme inactivation occurs, but the rate of inactivation is low relative to the rate of inactivation at 70°C. After some material loss of enzyme activity is observed after operating in the range from 50°C to 60°C or so, the temperature is raised at least about 5°C, either gradually, in increments of 2°–3°C or less, as needed to maintain the desired ketose level in the product, or alternatively, the temperature may be raised at least 5°C in a single step. Preferably, however, the increase in temperature for the second phase of operation is at least about 10°C, preferably through gradual or small incremental increases in operating temperature.

Among the objectives and advantages of the present invention are better enzyme stability, more desirable carbohydrate content of the isomerized product, improved efficiency as compared to batch conversions, and operating economy.

ASSAY OF ISOMERASE ACTIVITY

The assay procedure involves making a spectrophotometric determination of the ketose produced from a glucose solution under a standardized set of conditions. A stock solution is made up in the following manner:

Table 1

| Stock Solution for Assay | |
|---|---|
| Component | Amount |
| 0.1 M MgSO$_4$ 7H$_2$O | 1 ml. |
| 0.01 M CoCl$_2$ 6H$_2$O | 1 ml. |
| 1 M Phosphate buffer, pH 7.5 | 0.5 ml. |
| Anhydrous D-glucose | 1.44 grams |
| Distilled water | To make up a total volume of 7.5 ml. |

The enzyme preparation to be assayed is first sonicated or otherwise treated as necessary to put the enzyme in a form suitable for assay and then is diluted to contain from 1 to 6 isomerase units per ml.

An enzymatic isomerization is conducted by adding 1 ml. of the enzyme preparation to 3 ml. of the stock solution, and incubating for 30 minutes at 60°C. At the end of the incubation period, a 1 ml. aliquot is taken and quenched in a 9 ml. volume of 0.5 N perchloric acid. The quenched aliquot is then diluted to a total volume of 250 ml. As a control, for comparative purposes, a glucose blank is also run by substituting 1 ml. of water for the 1 ml. of the enzyme preparation in solution form, at the beginning of the incubation period.

The ketose is then determined by a cysteine-sulfuric acid method. For the purposes of this assay, one isomerase unit is defined as the amount of enzyme activity that is required to produce one micromole of levulose per minute under the isomerization conditions described.

DETAILED DESCRIPTION OF THE INVENTION

EXAMPLE 1

Continuous Isomerization Utilizing A fixed Bed of Microbial Cells: Single Step Temperature Adjustment For this demonstration of the invention, a jacketed column was used. The jacket was connected to a source of hot water, for controlling column temperature during isomerization.

A strain of a microorganism of the Streptomyces genus, that is recognized as a good isomerase producer, was grown under submerged, aerobic conditions on a medium containing xylose, to produce intracellular isomerase.

After fermentation, magnesium hydroxide was added to the fermenter broth in the ratio of two parts by weight of magnesium hydroxide for each one part by weight of the cell mass in the broth. The slurry thus obtained was filtered, and the filter cake was then dried in an open pan at room temperature. The activity of the dry enzyme preparation thus obtained was 330 units per gram.

The dry enzyme preparation was dispersed in a 50% W/V solution of dextrose. The slurry was then placed in the jacketed column, and as the slurry was added to the column, small glass beads, approximately 3 mm. in diameter, were added simultaneously. The glass beads served as a support and also prevented the enzyme preparation from packing and thus plugging up the column. In this fashion, approximately 750 units of the enzyme were charged to the column.

A dextrose syrup at 50% W/V concentration was adjusted to a PH in the range from 7.0 to 7.5 by adding magnesium hydroxide. The syrup was sparged with nitrogen, and was then fed to the top of the column under a nitrogen atmosphere.

The isomerized product was collected in aliquots of 15 ml., in test tubes. The test tubes each contained about 5 ml. of 0.5 N perchloric acid to inactivate any soluble isomerase that might be present in the product.

The temperature of the column was maintained at about 60°C during an initial phase of operation. The flow rate of dextrose solution through the column was maintained at a substantially uniform rate, and the ketose content of the effluent was 40% to 50% on a dry solids basis.

The isomerization was conducted in this manner for nine days before a substantial decrease in enzyme activity became apparent as evidenced by a dropping off in the ketose value observed in the effluent. During that initial phase of operation, the average ketose content of the effluent was 38.7%.

At the end of this initial phase of operation, the temperature of the column was increased (from the initial level of 60°C) to 70°C in a single step. Isomerization was then continued, at the increased temperature, for an additional period of 24 hours. The ketose content of the product averaged out at about 49%, for the second phase of operation. The results are summarized below in Table 2.

Table 2

Continuous Isomerization:
Single Step Temperature Adjustment

| | | | Output of approximately 42% d.b. Levulose Product (lbs. d.s. per cu. ft. of bed) | |
|---|---|---|---|---|
| Time | Temperature | Throughput Bed Volumes | | |
| Days | °C | per hour | Expected at 60°C | Obtained |
| 1 | 60 | 1.27 | 951 | 951 |
| 2 | 60 | 1.27 | 951 | 951 |
| 3 | 60 | 1.27 | 951 | 951 |
| 4 | 60 | 1.27 | 951 | 951 |
| 5 | 60 | 1.25 | 936 | 936 |
| 6 | 60 | 1.17 | 876 | 876 |
| 7 | 60 | 1.10 | 823 | 823 |
| 8 | 60 | 1.03 | 771 | 771 |
| 9 | 70 | 1.65 | 734 | 1235 |
| 10 | 70 | 1.65 | 681 | 1235 |

When the isomerization was repeated with an enzyme preparation prepared from a mixture of diatomaceous earth with the microbial cells, closely comparable results were obtained.

EXAMPLE 2

Continuous Isomerization Utilizing A Fixed Bed: Small Step Temperature Adjustments Intracellular isomerase was produced by growing a streptomyces culture under submerged, aerobic conditions on a xylose-containing medium.

At the end of the fermentation, diatomaceouos earth filter aid was added to the fermentation liquor in the ratio of 2 parts of the filter aid to 1 part of the microorganism cells, dry cell weight. The cell-diatomaceous earth mixture was separated by filtration, washed, and dried, for use as the enzyme preparation.

This enzyme preparation was suspended in dextrose solution and fed into a jacketed column. The lower outlet of the column was connected to a vacuum source to obtain a compact bed. When filled, the column contained 22 lbs. (dry weight) of the enzyme preparation (i.e., the cell-filter aid mixture) per cu. ft. of column volume.

Water at 60°C was passed through the jacket of the column. A solution containing 500 grams d.s. per liter of 95 D.E. starch hydrolysate containing 92% dextrose, dry basis, adjusted to pH 7.8 with magnesium hydroxide, was supplied continuously to the column, using pressure to control the flow rate. The flow rate was adjusted to maintain 42% (dry basis) levulose in the effluent from the column.

After 6 days of operation, the output volume rate had been dropped to 66% of the original value in order to maintain the 42% (dry basis) levulose content. Thereafter, the temperature was increased periodically, as shown in the table, to maintain the output rate of 42% levulose product at not less than 66% of the original output rate. As shown in the table, the total output quantity obtained in a period of 14 days by means of the increase in temperature was 41% greater than the total output which would have been obtained had the temperature been held constant at 60°C.

Table 3

Fixed Bed Isomerization With Small Step Temperature Increases

| Days | Temperature °C | Output of 42% d.b. Levulose Product (lbs. d.s. per cu. ft. of bed) | |
|---|---|---|---|
| | | Expected at 60°C | Obtained |
| 1 | 60 | 787 | 787 |
| 2 | 60 | 787 | 787 |
| 3 | 60 | 787 | 787 |
| 4 | 60 | 787 | 787 |
| 5 | 60 | 622 | 622 |
| 6 | 60 | 516 | 516 |
| 7 | 62 | 418 | 590 |
| 8 | 62 | 343 | 516 |
| 9 | 62 | 286 | 516 |
| 10 | 64 | 233 | 509 |
| 11 | 64 | 187 | 509 |
| 12 | 66 | 158 | 473 |
| 13 | 68 | 127 | 674 |
| 14 | 70 | 106 | 622 |
| | TOTAL | 6144 | 8695 |

EXAMPLE 3

Batch Isomerization Compared To Immobilized Fixed Bed Continuous Isomerization A fermentation is conducted with a microorganism of the Streptomyces genus, in a culture medium containing xylose, to produce isomerase. The cells are recovered from the fermentation broth by adding diatomaceous earth to the fermentation broth and filtering.

A portion of the wet filter cake is utilized an an enzyme preparation for conducting a batch isomerization with a 95 D.E. corn starch hydrolysate. Residence time in the stirred reactor is 50 hours at pH 6.25.

A separate portion of the same enzyme preparation is also employed as a fixed bed enzyme source, for conducting a continuous isomerization. Average residence time in the column is between one and two hours, at pH 8.

The batch isomerization is conducted at 70°C. The continuous isomerization is conducted at 60°C over an initial period of time, until substantial inactivation of the enzyme is observed, whereupon the column temperature is raised to 70°C.

The results are as reported in Table 4, below.

Table 4

| Batch vs. Column Isomerization Of A 95 D.E. Hydrolysate | | | |
|---|---|---|---|
| Batch, 50 Hrs., pH 6.25 | Feed | Isomerisate | Difference |
| Ash, % d.b. | 1.0 | 1.8 | 0.8 |
| Org. Acid, % d.b. | 0.05 | 0.08 | 0.03 |
| Color | 4 | 200 | 196 |
| Column, 1–2 Hrs., pH 8 | Feed | Isomerisate | Difference |
| Ash, % d.b. | 0.5 | 0.6 | 0.1 |
| Org. Acid, % d.b. | 0.03 | 0.04 | 0.01 |
| Color | 4 | 11 | 7 |

The batch isomerization is conducted at pH 6.25 because at pH values above 7.0, during the long residence time that is required for the batch process, the carbohydrate composition of the end product tends to be somewhat undesirable. The conditions employed for this comparison are believed to be reasonably close to the optimum for each type of process, and the comparison is highly favorable to the continuous process.

In terms of enzyme economy, the continuous process is much more efficient and involves the usage of a much lower amount of enzyme activity per unit of levulose product produced.

EXAMPLE 4

Stabilized Enzyme

As the isomerization temperature is increased, reaction rate increases, but so does inactivation of the isomerase. At some temperature, the rate of inactivation will exceed the increased reaction rate, and at this temperature, the product produced per unit time will decrease.

We have found a novel stabilizing technique for imparting enhanced thermal stability to isomerase. The use of our stabilized isomerase, coupled with temperature programmed operation, permits the production of high levulose syrups without excessive enzyme loss.

To produce stabilized isomerase, a very high purity enzyme is recovered from the cells. A Streptomyces-derived enzyme is preferred but the source microorganism may be any satisfactory producer of enzyme. The enzyme is placed in solution and is passed over a bed of particulate basic magnesium carbonate. The enzyme is efficiently absorbed and the product is a very stable, active form of the enzyme.

Operation at higher temperatures is conducive to higher levulose contents because the reaction rate is increased and the equilibrium levulose content is higher at the higher temperature. For example, equilibrium levulose contents at some elevated temperatures are listed below.

Table 5

| Isomerization Temperatures | Levulose Content, % Dry Basis Based on Initial Dextrose |
| --- | --- |
| 60°C | 51.2% |
| 70°C | 52.6% |
| 80°C | 54.0% |

When a column was packed with our stabilized enzyme, and a stream of a dextrose solution was passed through the column, good conversion was observed. Long enzyme life was obtained despite prolonged operations at 60°C and above, while levulose contents in the effluent were in at least 50% of total sugar present, dry basis. The isomerization was conducted at pH 8, and the product had exceptionally good color, was low in organic acid content, and was low in undesirable carbohydrates. The high operating pH promotes enzyme stability despite high operating temperatures, and the high temperatures permit a very short residence time in the column, thus minimizing investment requirements and inventory of in process material.

CONCLUSION

The invention can also be practised successfully with enzyme preparations of a different kind, although generally, the use of intact cells is preferred. Thus, in another demonstration of the invention, dried intact cells are converted to fine powder in a Waring blender. A buffer solution is prepared by dissolving a small amount of the surfactant Tween 80 in a 1.0 M glycine solution. The buffer solution is adjusted to pH 8.0 by adding a small amount of sodium hydroxide. A slurry is then prepared by adding 200 grams of the dry, fine powdered cells to 1,000 ml. of the buffer solution. The slurry is then filtered. 793 ml. of filtrate is recovered, having an activity of 17.5 units per ml.

One part of this enzyme solution is the anchored on a porous glass carrier having a high surface area and reactive silanol groups, as described in U.S. Pat. No. 3,556,945, granted Jan. 19, 1971. A second portion of the solution is absorbed on activated charcoal granules. Both forms of the enzyme can then be employed in practising continuous isomerization in accordance with the invention, utilizing the general techniques described above.

Advantages

One of the most important advantages of the practice of the present invention is lower enzyme cost per unit of levulose produced. As compared to batch isomerization, the same amount of enzyme, when utilized in accordance with the present invention, produces more levulose product than batch processing. Up to three times more product has been produced from a given amount of enzyme preparation, by practising the present invention, then is obtained when optimum processing batch techniques are employed.

In addition, there are many other important advantages. Generally speaking, continuous techniques utilizing an immobilized enzyme preparation permit much shorter isomerization times or residence times, that is, times of contact between the supply solution and the enzyme preparation. This means that the sugars, that are being processed, are subjected to the elevated processing temperature for a shorter time, and there is less thermal degradation. For these reasons, the finished product contains fewer color bodies, so that product color is superior and refining costs are lower. In addition, fewer organic acids are formed. Moreover, the carbohydrate composition of the end product is more desirable. Also, because of the shorter processing time, smaller inventories are required in process.

Immobilized Enzyme Technique

As disclosed in Example 4, another important aspect of the present invention pertains to an immobilized xylose isomerase preparation having improved retained isomerase activity and flow rate characteristics, as compared to the prior art enzyme preparations. Another related aspect of the present invention pertains to a novel and efficient means for recovering cell-free xylose isomerase from a fermentation broth. Still another related aspect of the present invention pertains to an improved process for continuously converting a dextrosecontaining solution to a levulose-bearing syrup, enzymatically, by use of the immobilized xylose isomerase.

The concept of binding enzymes to solid supports has become the subject of increasing interest. In general, these binding methods may be classified as follows:

1. Adsorption — binding to a solid support by physical or electrostatic forces as in the case of activated carbon or clay;
2. Ionic — attachment to ion exchange materials made from synthetic polymers, cellulose, starch, dextran, etc.;
3. Covalent bonding — coupling of enzymes to carrier through a functional group such as diazo, alkyl, peptide or silanyl groups;
4. Entrapment — immobilization by imbedding or inclusion in a gel structure of a hydrophilic polymeric material such as a polymer of an acrylamide or by the cell wall of a microorganism;
5. Cross-Linking — insolubilization by cross-linking the enzyme with a bifunctional agent; and
6. Flocculation — subjecting microbial cells containing the enzyme with a flocculating agent, such as anionic polyelectrolytes, cationic polyelectrolytes, and mineral hydrocolloids, such as described in Dutch Patent Specification 72/09532, published Jan. 11, 1973.

The prior art techniques have not enjoyed widespread acceptance in the industry. For example, activated charcoal, calcium carbonate, etc., are known to have a relatively high binding capacity for enzymes such as xylose isomerase. However, the resulting immobilized enzyme preparations are relatively inactive in respect of ability to convert dextrose-containing solutions to levlose-bearing syrups. In other words, many of the prior art immobilized enzymes have a relatively low effective isomerase activity. Furthermore, these immobilized enzymes of the prior art are generally unstable and typically have very short half-lives.

It has been proposed in U.S. Pat. No. 3,715,276 to Takasaki et al to utilize calcium carbonate, magnesium carbonate and several ion exchange resins to regulate the pH during prolonged enzymatic isomerization reactions of dextrose-containing solutions to levulose-bearing syrups. Takasaki et al utilized a xylose isomerase enzyme bound within the cells by a heat treatment. The enzyme did not become sorbed onto the pH regulating agent because it was bound within the cells. Furthermore, the pH regulating effect of calcium carbonate, magnesium carbonate and the ion exchange resins is only apparent when the isomerization is conducted over a relatively long period of time, i.e., a residence time of more than about four hours. In the case of enzymatic isomerizations where the residence time of the sugar solution exceeds about four hours, the formation of undesirable compounds occurs, one such compound being, for example, psicose. Since many industrial food uses for levulose-bearing syrups cannot tolerate psicose levels of more than 2% by weight, dry basis, and more often, 1% by weight, dry basis, prolonged residence time processes such as described in U.S. Pat. No. 3,715,276 are not commercially feasible.

It has now been found that cell-free, soluble xylose isomerase enzyme preparations, when contacted with basic magnesium carbonate, will become bound or sorbed, to thereby provide an immobilized enzyme preparation which has a high effective isomerase activity. Other related materials, such as calcium carbonate, do not provide a highly acitve and stable xylose isomerase. Also, intracellular xylose isomerase does not become sorbed onto basic magnesium carbonate.

The immobilized xylose isomerase preparation of the present invention is characterized as having a very high enzyme efficiency, whereby the sugar contact time necessary to produce a levulose-bearing syrup of at least about 45% by weight levulose from a dextrose-containing solution is generally less than about two hours. Due to the lower contact time occasioned by the improved retained enzyme activity of the composition of the present invention, the resulting levulose-bearing syrups have lower color, lower organic acid, and lower psicose content, i.e., generally less than about 1% by weight, dry basis, and quite often less than about 0.3% by weight, dry basis, psicose. These advantages are quite significant from the standpoint of capital investment and inventory in commercializing a process for enzymatically preparing levulose-bearing syrups from dextrose-containing solutions.

The stabilized xylose isomerase enzyme preparation of the invention is preferably prepared by contacting cell-free xylose isomerase with particulate basic magnesium carbonate. The particulate basic magnesium carbonate may be either in the form of a powder or a granular structure. However, the granular structure is preferred from the standpoint of flow properties when used in a deep bed converter. The stabilized enzyme preparation can be conveniently recovered by conventional means, such as by filtration and the like. Alternatively, the particulate basic magnesium carbonate may be first placed in a converter which is later to be used in the enzymatic isomerization reaction and, secondly, a solution of cell-free xylose isomerase may then be pumped through the column until no more enzyme is sorbed from the solution by the particulate basic magnesium carbonate. Following the preparation of the stabilized enzyme preparation, the converter is ready for use simply by supplying to the converter a dextrose-containing solution.

It will be understood that the xylose isomerase enzyme employed in this aspect of the invention can be either highly purified or crude. The enzyme can be purified by any conventional purification procedure, for example, fractional precipitation with sodium sulfate, ammonium sulfate or other material salts, selective adsorption and the like, differential heat inactivation of contaminating proteins by exposure of the product to increasing temperatures at different pHs, isoelectric precipitation, organic solvent precipitation with alcohols, DEAE-cellulose chromatography, and "Sephadex" gel filtration purification procedures, electrophoretic and ultracentrifuge separation, and the like.

The xylose isomerase enzyme preparation used is in its soluble form; in other words, the xylose isomerase is freed from the microbial cell where it is formed. The enzyme may be released from its cellular material by any conventional means, and the enzyme in the crude material may be then sorbed on the basic magnesium carbonate. The xylose isomerase thereupon becomes bound to the basic magnesium carbonate. The immobilized enzyme preparation can thereafter be recovered by filtration, centrifugation and the like, and then washed with a buffer. The filtered and washed immobilized enzyme composition can be used in its wet form, as is, or the cake can be dried by conventional drying techniques useful with enzyme preparations, such as by cell, rotary drum or spray drying or freeze drying techniques. Superior results are obtained, however, when the enzyme is purified before it is sorbed.

Prior to immobilization, the cell-free enzyme solution is preferably adjusted to a pH in the range of from about 7.5 to about 9.5 and, more preferably, in the range from about 8 to about 9. The immobilization can be conducted at room temperature (e.g., generally about 25°C), so as to prevent inactivation of the enzyme. However, higher temperatures can be tolerated if the enzyme solution is mixed with a dextrose-containing solution during immobilization. When the pH of the enzyme solution to be contacted with the basic magnesium carbonate is less than about 7, the basic magnesium carbonate will exhibit a tendency to decompose, and will not be suitable for use. Therefore, it is desirable thata the pH of the enzyme solution be maintained at about 7.5 or greater.

The enzyme solution will preferably have an activity of at least about 10 units/ml. (U/ml.) and may have an activity as high as 3,000 U/ml. Generally, the enzyme solution will have an activity of from about 50 U/ml. to about 200 U/ml. of isomerase enzymatic activity. (i.e., the enzylatic proteinaceous It has been found that the basic magnesium carbonate has a very high binding capacity for the xylose isomerase enzyme. In this connection, it has been found that the basic magnesium carbonate is capable of binding a quantity of the enzyme that would have an activity, if measured prior to sorption, equivalent to more than 150 units per gram (U/g.) of the bound enzyme (i.e.,the isomerase-basic magnesium carbonate complex). Generally, it has been observed that the amount of enzyme that is sorbed is an amount that would have 250 units of activity, if measured prior to sorption, per gram of the complex, and in practice, the number is often more than 500 U/g. of the complex. Unfortunately, as will be demostrated later in Example 8, not all of the original enxymatic activity is retained after complexing, even though all of the poteinaceous enzyme is in fact sorbed. The terms "bound isomerase" and "binding capacity", as used herein, are defined as units of isomerase, as measured in solution prior to sorption, bound to one gram of the complex, dry basis.

Surprisingly, in view of experience with other carriers, the immobilized xylsoe isomerase preparation of the invention has an extremely high "effective isomerase activity", i.e., the isomerase activity of the immobilized enzyme that will actually enzymatically convert dextrose into levulose. There are many materials which are capable of binding xylose isomerase, such as activated charcoal, calcium and zinc carbonate, and the like. However, when the enzyme is bound to these carriers, the enzyme's effectiveness, or effective activity, is diminished significantly. Quite often, immobilized enzyme complexes, made using these prior art carriers, have an effectiveness of less than 50% of the amount of activity that would be expected, based on the amount of isomerase actually bound or sorbed on the carrier. The immobilized xylose isomerase preparation of the present invention exhibits at least about 70% of the activity of the original isomerase that is bound to the carrier, and quite often more than 80%. In other words, the immobilized xylose isomerase exhibits more than 70% of the activity of the amount of isomerase that is actually bound to the basic magnesium carbonate.

The immobilized xylose isomerase preparation of the present invention, therefore, is characterized as having at least about 100 units of effective isomerase activity per gram of immobilized enzyme preparation, dry basis (i.e., 100 U/g. effective isomerase activity), and preferably at least about 175 U/g.

Another striking characteristic of the immobilized and stabilized enzyme preparation of the present invention is its long half-life. The enzyme preparation of the present invention is characterized as being capable of producing 45% levulose, d.b., at flow rates of greater than 0.5 bed volume/hour with an enzyme half-life in excess of 15 days.

The basic magnesium carbonate material employed for preparing the stabilized enzyme preparation of the invention is preferably a granular, porous substance of any desired particle size. The basic magnesium carbonate can be prepared by first preparing magnesium carbonate trihydrate slurry, dewatering the slurry to at least about 10% solids, and drying the resulting pasty mass. The resulting product has both a strong, crush-resistant structure and a marked affinity for soluble enzymes such as xylose isomerase.

Basic magnesium carbonate can also be prepared by the procedures and techniques described in U.S. Pat. Nos. 2,209,752; 2,209,753; and 2,209,754, the disclosures of which are incorporated herein by reference.

Some preferred types of basic magnesium carbonate suitable for the preparation of the immobilized enzyme preparation of the present invention may also be obtained commercially and some of these products have been identified as 4 $MgCO_3 \cdot Mg(OH)_2 \cdot 5H_2O$ (or 5 $MgO \cdot 4CO_2 \cdot 6H_2O$) having a molecular weight of about 485.74, an absolute density of about 2.16, a moisture content (110°C) of about 0.5% to about 2.3%, a bulk density, loose, of 3.5 to 8.0 pounds/cubic foot and a screen mesh size such that at least 99% (wet) passes through a 325 mesh screen and 3.2 $MgCO_3 \cdot Mg(OH)_2 \cdot 3.9H_2O$.

The stabilized, immobilized xylose isomerase enzyme preparation of the invention may be used in any process for the enzymatic conversion of dextrose-containing solutions to levulose-bearing syrups, including the temperature-programmed process described herein. The immobilized enzyme preparation is particularly suited for the continuous conversin of dextrose to levulose. The stabilized and immobilized enzyme preparation of the invention is also applicable to continuous enzymatic isomerization processes other than the temperature-programmed process described herein.

The advantages of the stabilized and immobilized enzyme preparation of the invention are particularly evident in terms of the high level of glucose isomerase activity present per gram of material, so that comparatively little contact time is required in preparing levulose-bearing syrups.

A preferred aspect of the invention therefore includes enzymatically converting dextrose to levulose by forming a reaction solution containing from about 20% to about 70% dextrose by weight and having a pH in the range of from about 7.5 to about 9.5, and a temperature of from about 30°C to about 90°C; and passing the reaction solution over a bed of the immobilized xylose isomerase having an effective isomerase activity of at least about 100 U/g. of the enzyme preparation.

Preferably, the reaction solution will contain from about 40% to about 60% dextrose by weight and the pH of the solution will be in the range of from about 8.2 to about 9.2. A reaction solution containing about 50% of dextrose, by weight, and a pH in the range of from about 8.4 to about 8.6 is most preferred.

Typically, the immobilized xylose isomerase preparation will have an effective isomerase activity of at least about 175 U/g. of immobilized enzyme preparation. The reaction temperature is preferably in the range of from about 50°C to about 75°C and a temperature of about 60°C is preferred.

The xylose isomerase enzyme is preferably derived from a microorganism belonging to the genus Streptomyces, and more preferably, a microorganism strain that is sselected from the group of mutant strains consisting of *S. olivochromogense*, ATCC No. 21713, *S. olivochromogenes*, ATCC No. 21714, and *S. oilvochromogenes*, ATCC No. 21715. The preparation of the latter mentioned strains is more specifically described in U.S. patent application Ser. No. 181,639, filed Sept. 17, 1971, now U.S. Pat. No. 3,813,318, to Armbruster et al, the disclosure of which is incorporated herein by reference.

The dextrose used for preparing the reaction solution may be dextrose in crystalline form, a re-melt, or a starch hydrolysate produced by either sequentially or concurrently enzymatically liquefying and saccharifying a starch-containing solution. Also suitable reaction solutions include starch hydrolysates which have been thinned or liquefied with an acid and, in a subsequent step, converted to a dextrose-containing solution, enzymatically by one or more enzymes. Preferred starch hydrolysates are prepared by converting an enzyme liquefied starch-containing solution with a combination of two enzymes, such as glucoamylase and 1,6-glucosidase enzymes.

The process for enzymatically converting dextrose to levulose employing the immobilized xylose isomerase enzyme preparation of the invention is most suitable in column reactors for the continuous enzymatic isomerization of dextrose to levulose, wherein the immobilized enzyme is packed in the column. The column may optionally contain additional materials to improve the flow rate of the reaction liquor, such as glass beads, filter aids, and the like. However, excellent flow rates are obtained by the use of granular basic magnesium carbonate having particle sizes greater than 40 mesh. Generally, the particle size of the preferred granular basic magnesium carbonate will be in the range of from about −12 to +20. The basic magnesium carbonate in granular form can be easily obtained by simply compacting and grinding commercially obtainable powdered basic magnesium carbonate in suitable equipment.

A preferred embodiment of the invention comprises utilizing more than one column, preferably at least three columns, containing the immobilized and stabilized xylose isomerase, positioned in series. Employing such a technique, a more efficient utilization of the immobilized enzyme preparation can be obtained. For example, higher flow rates can be employed. Also, when the first column in the series becomes inactivated, the feed liquor can be conveniently shifted to the second column, while the first column is being regenerated by contact with fresh, soluble xylose isomerase enzyme, and when the second column becomes inactivated, the feed liquor can be fed to the third column, initially and subsequently through the regenerated first column. In this manner, the process can be conducted continuously, without interruption. The immobilized xylose isomerase enzyme preparation can also be used in a pressure leaf filter comprising one or more flat filtering elements (leaves) supported vertically or horizontally in a cylindrical tank, such as manufactured by Industrial Filter Pump Manufacturing Company, Cicero, Illinois.

Since the basic magnesium carbonate containing the bound xylose isomerase enzyme must be maintained at an alkaline pH in order to prevent decomposition during the enzymatic isomerization reaction, the feed liquor containing dextrose should be pre-adjusted to the alkaline pH values indicated hereinabove, i.e., a pH of at least about 7.5, and preferably, a pH greater than 8.2. Due to the increased enzyme concentration and retained activity of the xylose isomerase-basic magnesium carbonate complex, its use in a continuous conversion reduces the time requirement necessary to provide a levulose syrup having 45% levulose, so that a change in pH due to the formation of organic acids in the converter is not evident. In other words, if the residence time or contact time in a column isomerization is less than two hours, and preferably, less than one hour, and the pH of the initial feed liquor is greater than 8.0, the formation of acid during the enzymatic isomerization is not apparent and, therefore, the pH of the feed syrup does not need to be regulated by an alkaline material, as demonstrated by the following example.

EXAMPLE 5

Continuous Enzymatic Conversion Of Dextrose To Levulose Using Immobilized Xylose Isomerase A granular basic magnesium carbonate material having a particle size in the range of −12 to +20 (55.8 grams) was placed in a column having a volume of 73.3 ml. A substantially pure, soluble, cell-free xylose isomerase enzyme derived from *S. olivochromogenes* ATCC No. 21713. in a 0.01 M $MgSO_4$ solution, having a 50 U/ml. activity, was contacted with granular basic magnesium carbonate to load the column with 5 million units/ft$^3$ of enzyme. The immobilized xylose isomerase enzyme had more than 100 U/g. of effective activity per gram of immobilized enzyme.

An aqueous dextrose feed liquor was then supplied to the column at 27° Baume (50%, d.s.). The feed liquor contained $MgCl_2$ (0.005 M with respect to $MgCl_2$). The pH of the feed was adjusted to the range from 8.4 to 8.8 with 4 N NaOH at 58°C.

The column containing the immobilized enzyme preparation was maintained at a temperature of 58°C. The residence time in the column was less than one hour. The initial bed volume per hour for the production of 45% levulose, dry basis ($BVH_{45}$ levulose) was about one.

The effluent syrup contained about 45% by weight levulose, dry basis, and less than about 0.3% by weight, dry basis, psicose. The following is an analysis of the pH of the feed syrup and effluent syrup after a prolonged continuous conversion campaign:

| Hours of Operation | Feed Syrup pH at 25°C | Effluent pH at 25°C |
|---|---|---|
| 261 | 8.60 | 8.60 |

The above experiment was repeated, except that the xylose isomerase was bound on an alumina carrier. The same dextrose feed liquor, pre-adjusted to a pH of 8.3 − 8.4 with 4 N NaOH, was pumped through the column, which was maintained at a temperature of 58°C, at a rate to provide 45% by weight levulose, dry basis, in the effluent. The residence time was less than one hour. The following is an analysis of the pH of the feed syrup and effluent syrup after a prolonged continuous conversion campaign:

| Hours of Operation | Feed Syrup pH at 25°C | Effluent pH at 25°C |
|---|---|---|
| 16 | 8.3 | 8.4 |
| 376 | 8.15 | 8.25 |
| 428 | 8.4 | 8.3 |

In the operation of a column where the residence time may exceed about four hours, it is particularly preferred to feed an alkaline material such as sodium hydroxide or $Mg(OH)_2$ solutions or a combination of the two into the column at different elevations. A suitable means for accomplishing this is to provide alkaline inlets at one or more places along the column, so that the pH of the reaction solution is maintained at a pH of at least about 7.5.

As another embodiment of the invention, the pH of the enzymatic isomerase reaction solution can be programmed by the use of one or more alkaline inlets along the column. In such a technique, the initial pH of the feed liquor can be about 7.5 or greater, preferably in the range of from about 7.5 to about 8.2 By introducing alkaline materials such as sodium hydroxide or $Mg(OH)_2$ or a combination of the two into the reaction solution via inlets along the column, the pH of the reaction solution can be conveniently increased to a value up to about 9.5. Preferably, the pH will be increased by a value of at least about 0.1 from supply liquor to effluent, although more beneficial results in terms of stability of the basic magnesium carrier and quality of the isomerase are realized when the pH is increased by a value of at least about 0.2.

EXAMPLE 6

Continuous Eznymatic Conversion Of Dextrose To Levulose Using Immobilized Xylose Isomerase A glass jacketed column 41 inches in length was used as the converter. The diameter of the enzyme bed was 1-1/16 inches. Water was pumped into the converter at the lower end at approximately two bed volumes per hour. Dry basic magnesium carbonate which had been screened through a 16 mesh and collected on a 30 mesh screen was then added into the converter through the top of the converter column. The particles of the basic magnesium carbonate settled toward the base of the converter, while the fine material in the basic magnesium carbonate was washed out the top of the column with the ascending water.

After the bed of basic magnesium carbonate particles was built, soluble xylose isomerase enzyme solution which was derived from a microorganism of the genus Streptomyces (one liter at an enzyme activity of 100 U/ml.) was pumped through the bed at room temperature. Based on the difference in enzyme activity of the solution before and after being cycled through the bed twice, 79,000 units of isomerase enzyme were bound in the basic magnesium carbonate bed, to provide a xylose isomerase-basic magnesium carbonate complex having an effective activity greater than 175 U/g.

Enzymatic isomerization of a dextrose solution to form a levulose-bearing syrup was conducted by passing through the column a solution containing 600 grams per liter of dextrose, at an initial pH of about 8.3, and at an initial flow rate of about 1.5 bed volumes per hour (approximately 800 ml. per hour). Aliquot samples were withdrawn periodically for analysis. For the first six hours of operation, the effluent product contained between 45.9% and 48.7% ketose, by weight. The flow rate to make a 45% by weight ketose product, dry basis, remained about one bed volume per hour or greater. The amount of psicose formed was less than 1% by weight, dry basis.

Based upon the results observed from the foregoing experiment, it was quite evident that the xylose isomerase-basic magnesium carbonate complex was quite active. The experiment was also indicative that the bound enzyme was active and also quite stable. Since the quality of a product from a continuous converter is satisfactory at a production rate of 0.5 bed volume per hour (BVH), the production time of this converter was 22 days and the half-life of the converter was 16–18 days. At an average production rate of 1.3 BVH at 45% levulose production for 17 days, the total product on a dry basis was 171,849 grams or 0.46 unit of enzyme per gram of product. This clearly represents a marked advantage of the invention, derived from the savings involved in utilization of the enzyme required to make the desired levulose product.

EXAMPLE 7

A commercially obtained basic magnesium carbonate powder was compacted and ground to a particle size in the range of from about −40 to +30. 31.7 grams of this granulated basic magnesium carbonate carrier were placed in a jacketed column filled with water. The bed had a volume of 53 ml. Water was pumped through the column from its lower end so that the coarser particles of the granular basic magnesium carbonate would settle to the base of the converter, while the fine material was washed out of the top of the column with the ascending water.

In a separate container, a solution was prepared containing a 95 D.E. starch hydrolysate at 50% solids and soluble enzyme. The xylose isomerase enzyme was one derived from Streptomyces and having 50 U/ml. of isomerase activity. The solution was brought up to 189 ml. Magnesium chloride ($MgCl_2$) was added to the solution to obtain a 0.005 M content with respect to $MgCl_2$. The pH was adjusted to 8.4 with 4 N sodium hydroxide.

The combination solution (starch hydrolysate and soluble enzyme) was pumped into the column containing the granular basic magnesium carbonate and circulated 2½ times through the column, so as to load the carrier with 5 million units per cubic foot of enzyme, at a temperature of 60°C. Once the solution containing the soluble enzyme and starch hydrolysate had been circulated into the column, the column thereupon was activated and ready for use to continuously convert a dextrose solution to a levulose-bearing syrup. The xylose isomerase-granular basic magnesium carbonate complex had an effective isomerase activity of greater than 175 U/g. of the complex.

A levulose-bearing syrup was continuously prepared in the column by pumping a solution containing a starch hydrolysate having a D.E. of about 95 and having a solids content of about 50%, dry basis. The starch hydrolysate that was pumped into the column was first treated with $MgCl_2$ to obtain a 0.005 M content based upon $MgCl_2$ and the pH of the solution was adjusted to 8.4 with 4 N NaOH. The isomerization was continuously conducted at a temperature of 60°C at an initial $BVH_{42}$ levulose of 1.6.

After 69 hours, the immobilized xylose isomerase in the column continued to convert dextrose into levulose, producing a product having a ketose content of 40.1%, dry basis, and a psicose content of 0.15% by weight, dry basis, to obtain an adjusted bed volume per hour equivalent to 1.8 $BVH_{42}$.

This experiment clearly demonstrates the stability and enzyme efficiency of the immobilized xylose isomerase of the present invention.

EXAMPLE 8

Comparative Example

Several alkaline earth metal carbonates were evaluated to compare their binding capacity ("bound isomerase") and effective isomerase activity ("retained isomerase activity") with particulate basic magnesium carbonate. In each instance, the carrier tested was contacted with a purified, cell-free xylose isomerase solution containing 2500 to 2600 U/ml. of glucose isomerase activity. The xylose isomerase used was derived from a microorganism of the genus Streptomyces (the strain *S. olivochromogenes*, ATCC No. 21713).

Each of the carriers was slurried in a 150 ml. beaker with 30 ml. of a solution consisting of 0.01 $MgSO_4 \cdot 7H_2O$. The slurry was adjusted to a pH of 8–9 with 0.1 N KOH. The purified xylose isomerase solution was then added to each carrier slurry to provide a total isomerase addition of about 2600 units of glucose isomerase activity. An additional amount of 0.01 $MgSO_4$ solution was added to each slurry of carrier and enzyme to attain a total volume of 50 ml. The pH of the solution was adjusted (if necessary) to 8 to 9. The beakers were covered and stirred at room temperature for 30 minutes to achieve maximum sorption of the enzyme on the respective carriers. The slurries were filtered and the carriers with the sorbed enzyme were washed with 100 ml. of the 0.01 M $MgSO_4$ solution. The filtrates and washings were combined and assayed for isomerase activity against the original isomerase activity added using a Technicon AutoAnalyzer.

The binding capacity or "bound isomerase" for the respective carriers was calculated by difference using the following formula:

$$\text{"Bound Isomerase" (BI), U/g., d.b.} = \frac{\text{Total Units Present} - \text{Total Units in Filtrate and Washing}}{\text{Grams of Carrier, d.b.}}$$

The "effective isomerase activity" (also referred to as "retained isomerase activity") of each of the alkaline earth metal carbonate carrier samples was also determined using the following procedure.

An aqueous solution containing 80 g. of dextrose (d.b.) and 13.3 mg. of $Mg(OH)_2$ per 100 ml. was prepared. The solution was stirred for at least one hour (preferably overnight) to equilibrate. The pH was adjusted to 8.5 at room temperature with 3 N KOH. 193.9 g. of substrate (about 150 ml.) was added to a 1-liter stainless steel beaker covered with a center-holed watch glass containing an additional hole near the edge. The sample was placed in a 60°C water bath, and stirred for 15 minutes, while maintaining a pH of 8.0 with 3 N KOH. The substrate was sparged with nitrogen at a moderate rate using a gas dispersion tube placed through the peripheral hole of the watch glass. A preweighed amount of xylose isomerase-basic magnesium complex containing from 1,000 to 3,000 units of bound isomerase was added using 50 ml. of 60°C water to transfer the material to the stainless steel beaker. This yielded a reaction mixture containing 60 g. of dextrose and 10 mg. of $Mg(OH)_2$ per 100 ml. and an isomerase dosage level of from 8.3 to 25.0 units per gram of dextrose. The reaction mixture was adjusted to pH 8.0, and digested for exactly two hours after enzyme addition. The material was filtered immediately by vacuum through an 11-cm. Whatman 541 paper and the pH of a 500 ml. portion of the filtrate was adjusted to about 2.5 with 1.0 N perchloric acid. The dry substance content of the inactivated sample was determined by refractive index measurement and the levulose concentration by using spectrophotometric or polarimetric procedures. From the amount of levulose produced, effective isomerase ("retained isomerase activity") activity was calculated using the following equation:

$$\text{Effective Activity, U/g, d.b. carrier} = \frac{V}{C} \times 26.46 \times \frac{51.2}{\log 51.2-L}$$

where:
V = reaction volume, ml.;
C = carrier, g., d.g.; and
L = levulose produced, % d.b.

The details and results of the specific tests are set forth in the following Table:

TABLE 6

| Carrier | Substrate Concentration g., d.s. 100 ml. | Solvent | Binding Capacity "Bound Isomerase Activity" (U/g., d.b.) | Effective Isomerase Activity (U/g., d.b.) | % Of Original Activity |
|---|---|---|---|---|---|
| $ZnCO_3$ | 60 | $MgSO_4$ | 515 | 252 | 48.9 |
| $CaCO_3$ | 60 | $MgSO_4$ | 368 | 54 | 14.7 |
| $BaCO_3$ | 60 | $MgSO_4$ | 38 | 75 | — |
| Basic[1] $MgCO_3$ | 60 | $MgSO_4$ | 412 | 294 | 71.4 |

[1] Basic Magnesium Carbonate having the formula $4 MgCO_3 \cdot Mg(OH)_2 \cdot 5H_2O$.

As it can be seen from the above data, there is a great deal of unpredictability in the binding capacity (also defined as "bound isomerase") and effective isomerase activity for the alkaline earth metal carbonates. It is particularly significant that $BaCO_3$ has an extremely low "bound isomerase" capability. While $ZnCO_3$ and $CaCO_3$ complexes with isomerase exhibit reasonable "bound isomerase activity", the complexes of both compounds exhibit a relatively low "effective isomerase activity" or ability to isomerase dextrose to levulose as compared to the xylose isomerase-basic magnesium carbonate complex of the present invention.

Not wishing to be bound to any theory, it is postulated that the relatively low "effective isomerase activity" occurs with respect to these salts ($ZnCO_3$ and $CaCO_3$) because the isomerase is bound so tightly that its conformation is changed and/or the isomerase is not accessible to the substrate due to the manner the isomerase is bound to the salt. In any event, it is unexpected that basic magnesium carbonate is capable of having a relatively high binding capacity in addition to a high "effective isomerase activity". The combination of these two features, together, provides a number of important advantages from the standpoint of more stability and longer half-life of the immobilized enzyme and greater enzyme efficiency. The enzyme efficiencies normally range from 0.30 to about 0.70. Thus, a deep bed column with an enzyme loading of 6 MM units/$ft^3$ (the amount of enzyme activity in the bed (units/g.) divided by the volume of the bed (lbs./$ft^3$)) and an enzyme efficiency of 0.6 would have an initial column production rate of 3.6 BVH at 45% ketose ($BVH_{45}$), wherein BVH is the supply rate divided by the bed volume.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention.

What is claimed is:

1. A method for recovering xylose isomerase from a fermentation broth comprising:
    contacting a fermentation broth containing xylose isomerase which is contained in the microbial cells where it is formed with basic magnesium carbonate and in a subsequent step, releasing the xylose isomerase from its microbial cells in the presence of basic magnesium carbonate to thereby sorb the sylose isomerase on the basic magnesium carbonate.

2. The method of claim 1, wherein the basic magnesium carbonate is a granular, porous substance.

3. The method of claim 1, wherein the xylose isomerase is derived from a microorganism of the genus Streptomyces.

4. The method of claim 1, wherein the xylose isomerase is derived from a microorganism selected from the group of strains consisting of *Streptomyces olivochromogenes* ATCC No. 21,713; *Streptomyces olivochromogenes* ATCC No. 21,714, and *Streptomyces olivochromogenes* ATCC No. 21,175.

5. The method of claim 1, wherein the sorbed xylose isomerase is placed in a column isomerization reactor.

6. The method of claim 1, wherein the sorbed xylose isomerase is placed in a pressure leaf filter comprising one or more filtering elements or leaves supported vertically or horizontally in a cylindrical tank.

7. The method of claim 6, wherein a glucose-containing solution is pumped through the filtering elements or leaves containing the sorbed xylose isomerase to enzymatically isomerize the glucose to levulose.

8. The method of claim 7, wherein the levulose product so produced contains less than 0.3%, dry basis, psicose and less than 1%, dry basis, ash.

* * * * *